United States Patent [19]

Woodle et al.

[11] Patent Number: 5,013,556
[45] Date of Patent: May 7, 1991

[54] LIPOSOMES WITH ENHANCED CIRCULATION TIME

[75] Inventors: Martin C. Woodle, Menlo Park; Francis J. Martin, San Francisco; Annie Yau-Young, Los Altos; Carl T. Redemann, Walnut Creek, all of Calif.

[73] Assignee: Liposome Technology, Inc., Menlo Park, Calif.

[21] Appl. No.: 425,224

[22] Filed: Oct. 20, 1989

[51] Int. Cl.$^5$ ............................................... A61K 37/22
[52] U.S. Cl. ..................................... 424/450; 424/1.1; 264/4.3
[58] Field of Search .................... 424/450, 1.1; 264/4.3

[56] References Cited

U.S. PATENT DOCUMENTS

| | | |
|---|---|---|
| 4,534,899 | 8/1985 | Sears . |
| 4,837,028 | 6/1989 | Allen ................................... 424/450 |
| 4,885,172 | 12/1989 | Bally et al. .......................... 424/450 |
| 4,904,479 | 2/1990 | Illum . |
| 4,920,016 | 4/1990 | Allen et al. . |

OTHER PUBLICATIONS

"Targeting of Colloidal Particles to the Bone Marrow", Illum et al., Life Sciences, vol. 44, pp. 1553-1560, (1987).

"Effect of the Nonionic Surfactant Poloxamer 338 on the Fate and Deposition of Polystyrene Microspheres Following Intravenous Administration", Illum et al., J. Pharm. Sci., vol. 72, No. 9, (Sep. 83).

"The Organ Distribution and Circulation Time of Intravensously Injected Collodial Carriers Sterically Stabilized with a Blockcopolymer-Poloxamine 908", Illum et al., Life Sciences, vol. 40, pp. 367-374, (1987).

"The Organ Uptake of Intravenously Administered Colloidal Particles Can Be Altered Using a Non-Ionic Surfactant (Poloxamer 338)", Illum et al., Federation of European Biochem. Soc's, (Elsevier Science Publishers B.V.), vol. 167, No. 1, (Feb. 1984).

Primary Examiner—Thurman K. Page
Assistant Examiner—P. L. Prater
Attorney, Agent, or Firm—Peter J. Dehlinger

[57] ABSTRACT

A liposome composition which contains between 1-20 mole percent of an amphipathic lipid derivatized with a polyalkylether, as exemplified by phosphatidylethanolamine derivatized with polyethyleneglycol. The derivatized lipid enchances the circulation time of the liposomes severalfold, and this enhancement is achieved with either fluid or membrane-rigidifying liposome components. Also disclosed are methods for delivering a drug for slow release from the bloodstream, and for targeting a selected tissue or cells with liposomes, via the bloodstream.

34 Claims, 4 Drawing Sheets

LIPOSOMES WITH ENHANCED CIRCULATION TIME

1. FIELD OF THE INVENTION

The present invention relates to liposome therapeutic compositions, and, more particularly, to liposome compositions which have enhanced circulation time when administered intravenously.

2. REFERENCES

Allen, T. M., (1981) Biochem. Biophys. Acta 640. 385397.

Allen, T. M., and Everest, J. (1983) J. Pharmacol. Exp. Therap. 226. 539-544.

Altura, B. M. (1980) Adv. Microcirc. 9, 252-294.

Alving, C. R. (1984) Biochem. Soc. Trans. 12. 342344.

Ashwell, G., and Morell, A. G. (1974) Adv. Enzymology 41, 99-128.

Czop, J. K. (1978) Proc. Natl. Acad. Sci. USA 75:3831.

Durocher, J. P., et al. (1975) Blood 45:11.

Ellens, H., et al. (1981) Biochim. Biophys. Acta 674. 10-18.

Gabizon, A., et al., J. Liposome Research 1:123 (1988).

Gregoriadis, G., and Ryman, B. E. (1972) Eur. J. Biochem. 24, 485-491.

Gregoriadis, G., and Neerunjun, D. (1974) Eur. J. Biochem. 47, 179-185.

Gregoriadis, G., and Senior, J. (1980) FEBS Lett. 119, 43-46.

Greenberg, J. P., et al (1979) Blood 53:916.

Hakomori, S. (1981) Ann. Rev. Biochem. 50, 733-764.

Hwang, K. J., et al. (1980) Proc. Natl. Acad. Sci. USA 77:4030.

Jonah, M. M., et al. (1975) Biochem. Biophys. Acta 401, 336-348.

Juliano, R. L., and Stamp, D. (1975) Biochem. Biophys. Res. Commun. 63. 651-658.

Karlsson, K. A. (1982) In: Biological Membranes, Vol. 4, D. Chapman (ed.) Academic Press, N.Y., pp. 1-74.

Kimelberg, H. K., et al. (1976) Cancer Res. 36, 2949-2957.

Lee, K. C., et al., J. Immunology 125:86 (1980).

Lopez-Berestein, G., et al. (1984) Cancer Res. 44, 375-378.

Okada, N. (1982) Nature 299:261.

Poznansky, M. J., and Juliano, R. L. (1984) Pharmacol. Rev. 36. 277-336.

Richardson, V. J., et al. (1979) Br. J. Cancer 40, 3543.

Saba, T. M. (1970) Arch. Intern. Med. 126. 1031-1052.

Schaver, R. (1982) Adv. Carbohydrate Chem. Biochem. 40:131.

Scherphof, T., et al. (1978) Biochim. Biophys. Acta 542, 296-307.

Senior, J., and Gregoriadis, G. (1982) FEBS Lett. 145, 109-114.

Senior, J., et al. (1985) Biochim. Biophys. Acta 839, 1-8.

Szoka, F., Jr., et al. (1978) Proc. Natl. Acad. Sci. USA 75:4194.

Szoka, F., Jr., et al. (1980) Ann. Rev. Biophys. Bioeng. 9:467.

Woodruff, J. J., et al. (1969) J. Exp. Med. 129:551.

3. BACKGROUND OF THE INVENTION

Liposome delivery systems have been proposed for a variety of drugs. For use in drug delivery via the bloodstream, liposomes have the potential of providing a controlled "depot" release of a liposome-entrapped drug over an extended time period, and of reducing toxic side effects of the drug, by limiting the concentration of free drug in the bloodstream. Liposome/drug compositions can also increase the convenience of therapy by allowing higher drug dosage and less frequent drug administration. Liposome drug delivery systems are reviewed generally in Poznansky et al.

One limitation of intravenous liposome drug delivery which has been recognized for many years is the rapid uptake of blood-circulating liposomes by the mononuclear phagocytic system (MPS), also referred to as the reticuloendothelial system (RES). This system, which consists of the circulating macrophages and the fixed macrophages of the liver (Kupffer cells), spleen, lungs, and bone marrow, removes foreign particulate matter, including liposomes, from blood circulation with a half life on the order of minutes (Saba). Liposomes, one of the most extensively investigated particulate drug carriers, are removed from circulation primarily by Kupffer cells of the liver and to a lesser extent by other macrophage populations.

A variety of studies on factors which effect liposome uptake by the RES have been reported. Early experiments, using heterogeneous preparations of multilamellar liposomes (MLV) containing phosphatidylcholine (PC) and cholesterol (CH) as their principal lipid constituents, demonstrated that these liposomes are rapidly removed from circulation by uptake into liver and spleen in a biphasic process with an initial rapid uptake followed by a slow phase of uptake (Gregoriadis, 1974; Jonah; Gregoriadis, 1972; Juliano). Half-time for removal of MLV from circulation was on the order of 5-15 min. following intravenous (IV) injection. Negatively charged liposomes are removed more rapidly from circulation than neutral or positively charged liposomes. Small unilamellar liposomes (SUV) are cleared with half-lives approximately three-to four-fold slower than MLV (Juliano; Allen, 1983). Uptake of liposomes by liver and spleen occurs at similar rates in several species, including mouse, rat, monkey, and human (Gregoriadis, 1974; Jonah; Kimelberg, 1976; Juliano; Richardson; Lopez-Berestein).

Liposomes which are capable of evading the RES would have two important benefits. One is the increased liposome circulation time in the blood, which would both increase the pharmacokinetic benefits of slow drug release in the bloodstream, and also provide greater opportunity for tissue targeting where the liver, spleen, and lungs are not involved. The second benefit is decreased liposome loading of the RES. In addition to the role of the RES in removing foreign particles, the RES is involved in several other functions, including host defense against pathogenic microorganisms, parasites, and tumor cells, host responses to endotoxins and hemorrhagic shock, drug response, and responses to circulating immune complexes (Saba, Altura). It is important, therefore, in liposome administration via the bloodstream, to avoid compromising the RES seriously, by massive short-term or accumulated liposome uptake.

One approach which has been proposed is to increase liposome circulation time by increasing liposome stability in serum. This approach is based on studies which have shown that factors which decrease leakage of liposome contents in plasma also decrease the rate of uptake of liposomes by the RES (Allen, 1983; Gregoriadis, 1980; Allen, 1981; Senior, 1982). One factor contributing to this effect appears to be bilayer rigidity, which renders the liposomes more resistant to the destabilizing effects of serum components, in particular high density lipoproteins (Allen, 1981; Scherphof). Thus, inclusion of cholesterol in the liposomal bilayer can reduce the rate of uptake by the RES (Gregoriadis, 1980; Hwang; Senior, 1985), and solid liposomes such as those composed of distearoylphosphatidylcholine (DSPC) or containing large amounts of sphingomyelin (SM) show decreased rate and extent of uptake into liver (Allen, 1983; Ellens; Senior, 1982; Hwang). However, this approach appears to have a limited potential for increasing liposome circulation times in the bloodstream.

Efforts designed to enhance liposome circulation time, by modifying the liposome outer surface to mimic that of the red blood cell, have also been reported. The role of cell surface carbohydrates in cellular recognition phenomena is widely appreciated (Ashwell, Hakomori, Karlsson). The chemistry, metabolism, and biological functions of sialic acid have been reviewed (Schauer). Surface sialic acid, which is carried by gangliosides, and glycoproteins such as glycophorin, plays an important role in the survival of erythrocytes, thrombocytes, and lymphocytes in circulation. Enzymatic removal of sialic acid, which exposes terminal galactose residues, results in rapid removal of erythrocytes from circulation, and uptake into Kupffer cells of the liver (Durocher). Desialylation of thrombocytes (Greenberg) and lymphocytes (Woodruff) also results in their rapid removal by the liver.

Although desialylated erythrocytes will bind to Kupffer cells or peritoneal macrophages in vitro in the absence of serum, serum must be added in order for significant phagocytosis to occur. The nature of the serum components mediating endocytosis is speculative, but immunoglobin[globulin?] and complement (C3b) are thought to be involved. Czop et al. (Czop) have shown that sheep erythrocytes, which are not normally phagocytosed by human monocytes, will bind C3b and be phagocytosed upon desialylation. Okada et al. (Okada) have demonstrated that sialyglycolipids on liposome membranes restrict activation of the alternative complement pathway and that removal of the terminal sialic acid from the glycolipids abolishes this restricting capacity and results in activation of the alternative complement pathway. Sialic acid, therefore, may be functioning as a nonrecognition molecule on cell membranes partly through its ability to prevent binding of C3b, thus preventing phagocytosis via the alternative complement pathway. Other immune factors may also be involved in liposome phagocytosis. Alving has reported that 50% of the test sera from individual humans contain naturally occurring "anti-liposome" antibodies which mediated complement-dependent immune damage to liposomes.

The observations reported above suggest that surface sialic acid, and/or other red-cell surface agents, incorporated into liposomes, for example, in the form of ganglioside or glycophorin, may lead to increased circulation half-lives of liposomes. This approach is proposed, for example, in U.S. Pat. No. 4,501,728 for "Masking of Liposomes from RES Recognition."

Co-owned U.S. Pat. No. 4,837,028 discloses a liposome composition which shows significantly enhanced circulation half-life, as measured by blood/RES ratios 2 hours after intravenous administration. Two factors were required for achieving high blood/RES ratios. The first was the presence of the specific ganglioside $GM_1$, which produced blood/RES ratios significantly greater than those seen with a variety of other glycosides and/or negatively charged lipids which were examined. Secondly, high blood/RES ratios were only observed in the liposomes composed predominantly of membrane-rigidifying lipids, such as sphingomyelin or phospholipids with saturated acyl chains.

The results reported in the above-cited patent suggest that a combination of specific surface molecules, such as $GM_1$, and rigid membrane lipid components, may be required for achieving effective liposome evasion of the RES. However, it is not known from these studies whether other surface molecules would be effective in enhancing liposome blood circulation times, and, if so, whether such molecules would be practical for use in liposomes designed for intravenous injection in humans. Further, the requirement for membrane-rigidifying membrane components may present limitations in liposome formulation methods, and also limit the ability to control the rate of drug release from circulating liposomes, by varying the "fluidity" of the lipids making up the liposomes.

4. SUMMARY OF THE INVENTION

One general object of the invention is to provide a liposome composition characterized by enhanced circulation time in the bloodstream.

Another object of the invention is to provide such a composition in liposomes composed of either fluid or rigid vesicle-forming lipids.

Still another object of the invention is to provide a method which utilizes the liposome composition to deliver drugs to a target tissue accessible via the bloodstream.

The invention includes, in one aspect, a liposome composition for administering a drug via the bloodstream. The composition includes liposomes containing the drug in liposome-entrapped form, and between 1–20 mole percent of an amphipathic lipid derivatized with a polyalkylether. One preferred amphipathic lipid is a phospholipid, such as phosphatidylethanolamine, derivatized with polyethyleneglycol. The liposomes in the composition preferably have a selected average size in the size range between about 0.05 and 0.5 microns.

The vesicle-forming lipids making up the liposomes may be predominantly rigid lipid components, such as sphingomyelin, or fluid lipids, such as phospholipids with predominantly unsaturated acyl chains.

In one embodiment, the polyalkylether is derivatized to the amphipathic lipid through an esterase- or peptidase-sensitive linkage. The rate of clearance of the liposomes from the bloodstream can then be modulated according to the rate of release of polyalkylesther groups from the liposome surface.

In another embodiment, the liposomes are formulated to contain surface-bound ligand molecules which are effective to bind specifically and with high affinity to ligand-binding molecules carried on the surface of specific target tissue or cells.

In another aspect, the invention includes a method of enhancing the blood-circulation time of liposomes administered intravenously. The enhanced circulation time is achieved by adding to the liposomes, in an amount between about 1-20 mole percent, an amphipathic lipid derivatized with a polyalkylether. The method is preferably effective to enhance the blood/RES ratio, 24 hours after intravenous administration, by up to tenfold or more over that observed with the same liposomes in the absence of the derivatized amphipathic lipid.

In still another aspect, the invention includes a method of administering a drug intravenously, for delayed drug release into the bloodstream. A suspension of liposomes containing the drug in liposome-entrapped form, and between about 1-20 mole percent of an amphipathic lipid derivatized with a polyalkylether, is administered parenterally, in an amount of the suspension containing a pharmacologically acceptable amount of the drug.

Also included in the invention is a method for delivering a drug selectively to a target tissue or cell type characterized by surface-bound tissue-specific ligand-binding molecules. A suspension of liposomes containing a surface-bound ligand effective to bind specifically and with high affinity to said ligand-binding molecule, and between 1-20 mole percent of an amphipathic lipid derivatized with a polyalkylether is administered parenterally. The target tissue may be a disease-related tissue, such as a solid tumor, or a circulating cell type, such as a virus-infected blood cell having virus-specific surface antigens.

A related aspect of the invention embraces a method of enhancing the uptake, by the reticuloendothelial system, of cells carrying surface-specific ligand-binding molecules which are characteristic of a disease state. The method is based on ligand-specific binding of liposomes containing between 1-20 mole percent of an amphipathic lipid derivatized with a polyalkylether, and a surface-bound ligand to the ligand-binding molecules on the cells.

These and other objects and features of the invention will become more fully apparent when the following detailed description of the invention is read in conjunction with the accompanying drawings.

DETAILED DESCRIPTION OF THE INVENTION DEFINITIONS

As used herein, the term:

"Polyalkylether" refers to polyethyleneglycol and related homopolymers, such as polymethylethyleneglycol, polyhydroxypropyleneglycol, polypropyleneglycol, polymethylpropyleneglycol, and polyhydroxypropyleneoxide, and to heteropolymers of small alkoxy monomers, such as a polyethetylene/polypropyleneglycol, such polymers having a molecular weight of at least about 120 daltons, and up to about 20,000 daltons.

"Amphipathic lipid" refers to any lipid having an amphipathic hydrophobic group, typically including two acyl hydrocarbon chains or a steroid group by which the lipid can be anchored in the outer lipid layer of a lipid bilayer, and a polar group which contains a reactive chamical group, such as an amine, acid, ester, aldehyde, or alcohol group by which the lipid can be derivatized to a polyalkylether.

"Amphipathic lipid derivatized with a polyalkylether" and "polyalkylether lipids" refers to an amphipathic lipid which is covalently joined, at its polar group, to a polyalkylether.

I. PREPARATION OF POLYALKYLETHER LIPIDS

Figure 1:
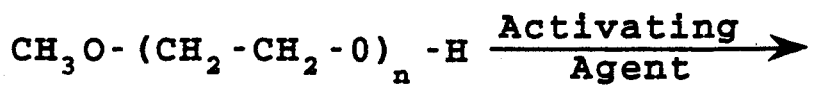
FIG. 1 illustrates a general reaction scheme for derivatizing an amphipathic lipid amine with a polyalkylether.
Figure 1:
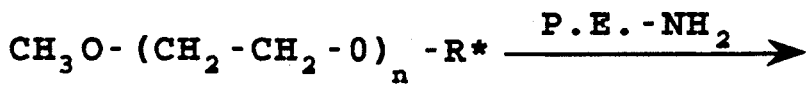
Figure 1:
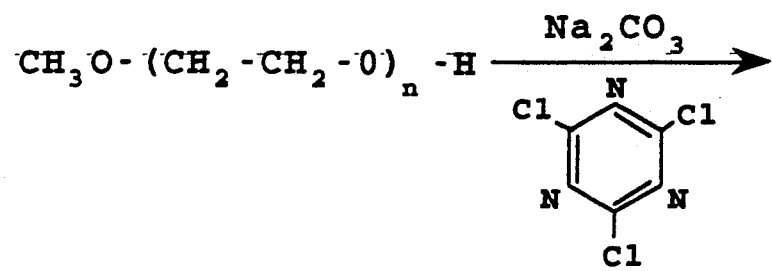

FIG. 1 shows a general reaction scheme for forming polyalkyl ethers. The polyalkyether which is employed, such as the polyethyleneglycol (PEG) molecule shown, is preferably capped by a methoxy, ethoxy or other unreactive group at one end. The polymer is activated at its other end by reaction with a suitable activating agent, such as cyanuric acid, carbonyl diimadozle, anhydride reagent, or the like, as described below. The activated compound is then reacted with a suitable amphipathic lipid, such as the phosphatidylethanolamine (PE) shown, to produce the derivatized lipid. Alternatively, the lipid group may be activated for reaction with the polyalkylether, or the two groups may be joined in a concerted coupling reaction, according to known coupling methods.

The polyalkylether, such as polyethyleneglycol or polypropyleneglycol, or the methoxy- or ethoxy-capped analogs, can be obtained commercially in a variety of polymer sizes, e.g., 120-20,000 dalton molecular weights. Alternatively, the homo- or heteropolymer can be formed by known polymer sysnthesis methods to achieve a desired monomeric composition and size. One preferred polyalkylether is PEG having a molecular weight between about 1,000 and 5,000 daltons.

The amphipathic lipid is preferably a vesicle-forming lipid having two hydrocarbon chains, typically acyl chains, and a polar head group. Included in this class are the phospholipids, such as phosphatidylcholine (PC), PE, phosphatidic acid (PA), phosphatidylinositol (PI), and sphingomyelin (SM), where the two hydrocarbon chains are typically between about 14-22 carbon atoms in length, and have varying degrees of unsaturation. Also included in this class are the glycolipids, such as cerebroside and gangliosides.

Another amphipathic lipid which may be employed is cholesterol and related sterols. In general, cholesterol may be less tightly anchored to a lipid bilayer membrane, particularly when derivatized with a high molecular weight polyalkylether, and therefore be less effective in promoting liposome evasion of the RES in the bloodstream. Similarly, single-chain lipids, such as long-chain fatty acids, may be derivatized with a polyalkylether, but provide less effective anchoring to the bilayer membrane than a lipid having two or more hydrocarbon chains.

According to one important feature of the invention, the amphipathic lipid may be a relatively fluid lipid, typically meaning that the lipid phase has a relatively low lipid melting temperature, e.g., at or below room temperature, or relatively rigid lipid, meaning that the lipid has a relatively high melting temperature, e.g., up to 50° C. As a rule, the more rigid, i.e., saturated lipids, contribute to greater membrane rigidity in a lipid bilayer structure and also contribute to greater bilayer stability in serum. Other lipid components, such as cholesterol, are also known to contribute to membrane rigidity and stability in lipid bilayer structures. Phospholipids whose acyl chains have a variety of degrees of saturation can be obtained commercially, or prepared according to known methods.

Figure 2:
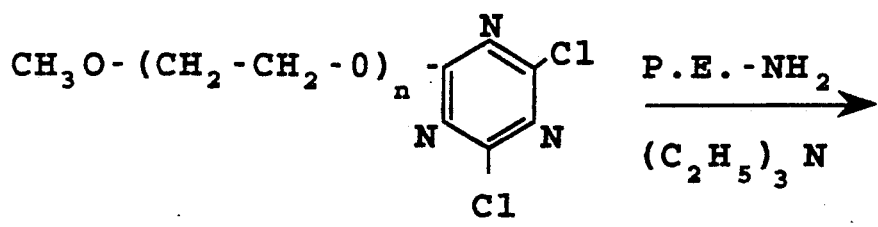
FIG. 2 is a reaction scheme for preparing phosphatidylethanolamine (PE) derivatized with polyethyleneglycol via a cyanuric chloride linking agent.
Figure 2:
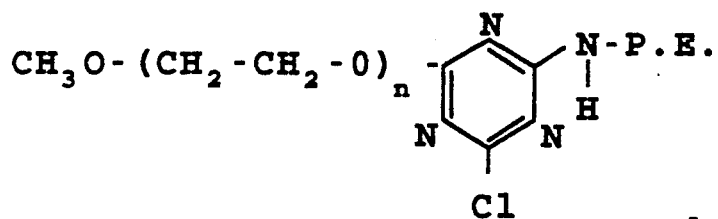

FIG. 2 shows a reaction scheme for producing a PE-PEG lipid in which the PEG is derivatized to PE through a cyanuric chloride group. Details of the reaction are provided in Example 1. Briefly, methoxy-capped PEG is activated with cyanuric chloride in the presence in sodium carbonate under conditions which produced the activated PEG compound shown at the top in the figure. This material is purified to remove unreacted cyanuric acid. The activated PEG compound is reacted with PE in the presence of triethyl amine to produce the desired PE-PEG compound shown at the bottom in the figure. The yield is about 8-10% with respect to initial quantities of PEG.

The method just described may be applied to a variety of lipid amines, including PE, cholesteryl amine, and glycolipids with sugar-amine groups.

Figure 3:
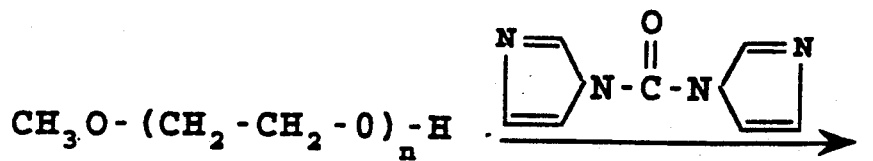
FIG. 3 illustrates a reaction scheme for preparing phosphatidylethanolamine (PE) derivatized with polyethyleneglycol by means of a carbonyl diimidazole activating reagent.
Figure 3:
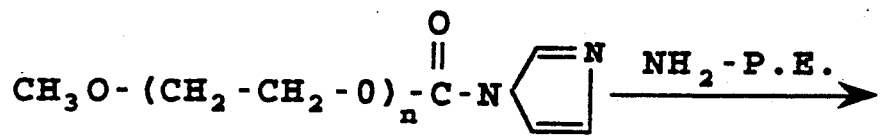
Figure 3:
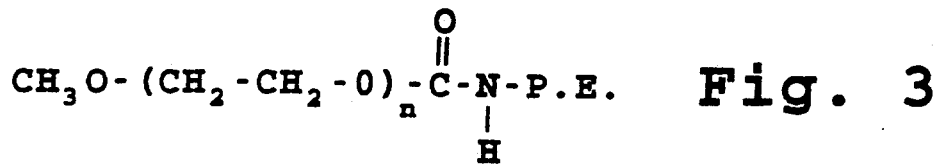

A second method of coupling a polyalkylether, such as capped PEG to a lipid amine is illustrated in FIG. 3. Here the capped PEG is activated with a carbonyl diimidazole coupling reagent, to form the activated imidazole compound shown at the center in FIG. 3. Reaction with a lipid amine, such as PE, leads to PEG coupling to the lipid through a carbamate linkage, as illustrated in the PEG-PE compound shown at the bottom in the figure. Details of the reaction are given in Example 2.

Figure 4:
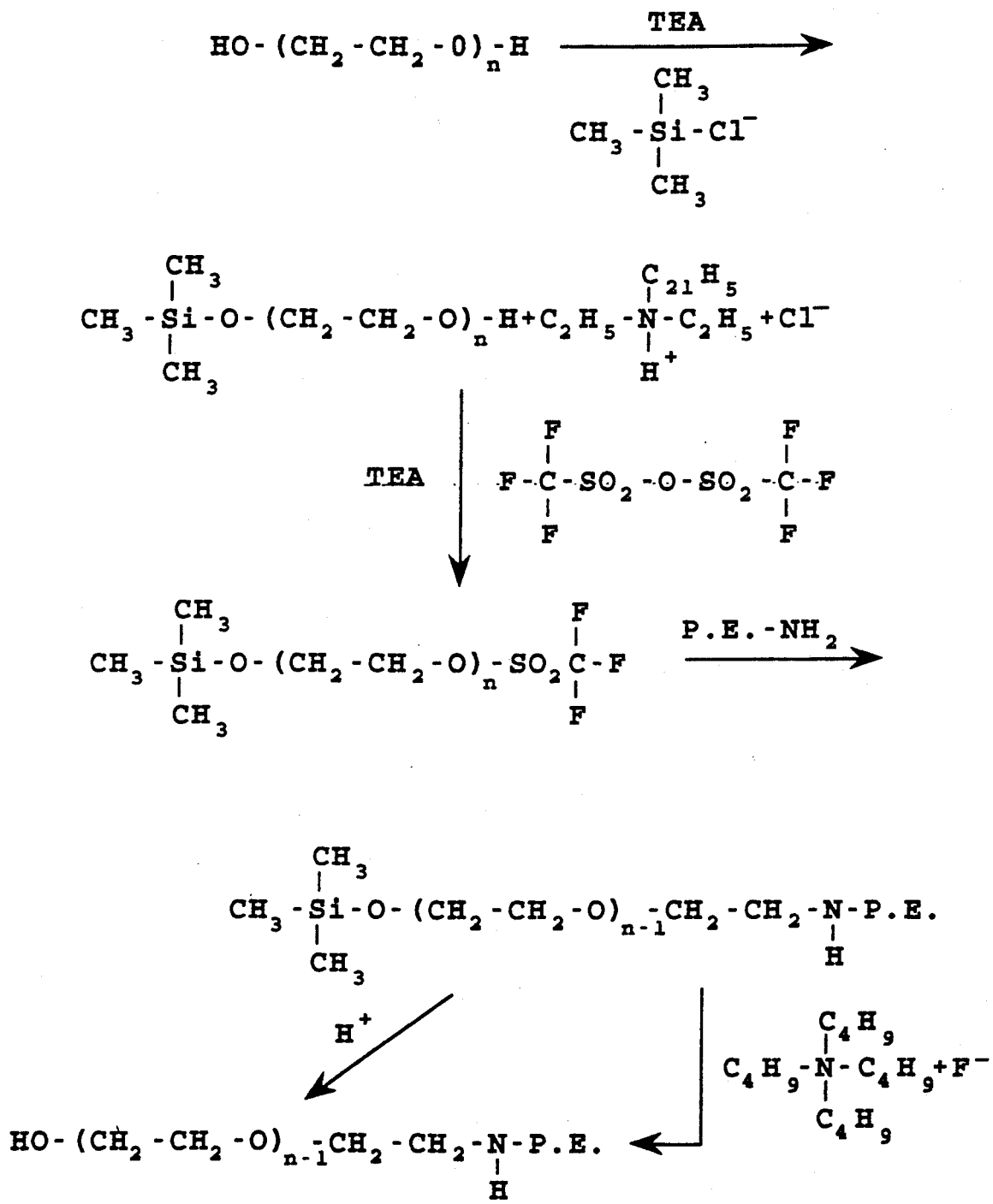
FIG. 4 illustrates a reaction scheme for preparing phosphatidylethanolamine (PE) derivatized with polyethyleneglycol by means of a trifluoromethane sulfonate reagent.

A third reaction method for coupling a capped polyalkylether to a lipid amine is shown in FIG. 4. Here a polyalkylether, as exemplified by PEG is first protected at its free OH. The end-protection reaction is shown at the top in the figure, and involves the reaction of trimethylsilylchloride with PEG in the presence of triethylamine. The protected PEG is then reacted with the anhydride of trifluoromethyl sulfonate to form PEG activated with trifluoromethyl sulfonate. Reaction of the activated compound with a lipid amine, such as PE, in the presence of triethylamine, gives the desired derivatized lipid product, such as the PEG-PE compound, in which the lipid amine group is coupled to the polyether through the terminal methylene carbon in the polyether polymer. The trimethylsilyl protective group can be released by acid treatment, as indicated at the lower left in the figure, or by reaction with a quaternary amine fluoride salt, such as the fluoride salt of tetrabutylamine.

It will be appreciated that a variety of known coupling reactions, in addition to those just described, are suitable for preparing polyalkyletheramine lipid derivatives for use in the liposome composition of the invention. For example, the sulfonate anhydride coupling reagent illustrated in FIG. 4 can be used to join an activated polyalkylether to the hydroxyl group of an amphipathic lipid, such as the 5'OH of cholesterol. Other reactive lipid groups, such as an acid or ester lipid group may also be used for coupling, according to known coupling methods. For example, the acid group of phosphatidic acid can be activated to form an active lipid anhydride, by reaction with a suitable anhydride, such as acetic anhydride, and the reactive lipid can then be joined to a protected polyalkylamine, e.g., by reaction in the presence of an isothiocyanate reagent.

Figure 5A:
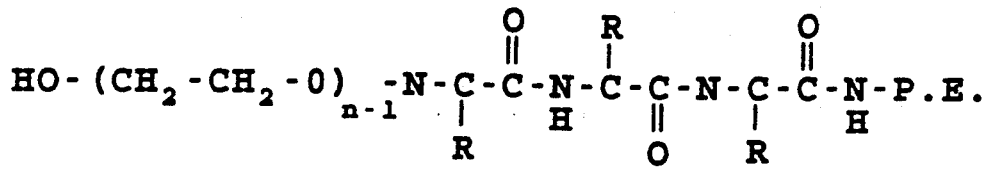
FIG. 5 illustrates an amphipathic lipid derivatized with polyethyleneglycol through a peptide (A), ester (B), and disulfide (C) linkage.
Figure 5B:
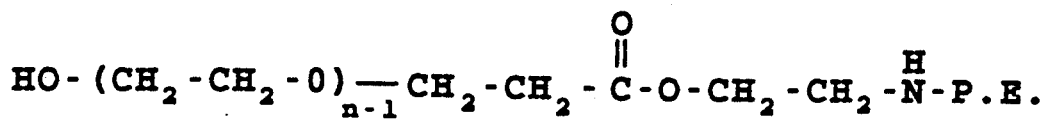
Figure 5C:
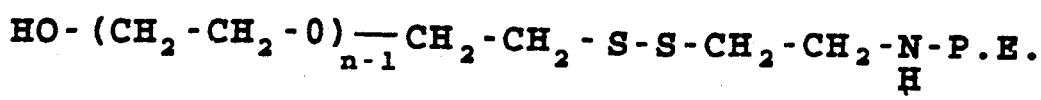

In another embodiment, the derivatized lipid components are prepared to include a labile lipid-polymer linkage, such as a peptide, ester, or disulfide linkage, which can be cleaved under selective physiological conditions, such as in the presence of peptidase or esterase enzyme present in the bloodstream. FIG. 5 shows exemplary lipids which are linked through (A) peptide, (B), ester, and (C), disulfide containing linkages. The peptide-linked compound can be prepared, for example, by first coupling a polyalkylether with the N-terminal amine of the tripeptide shown, e.g., via the reaction shown in FIG. 3. The peptide carboxyl group can then be coupled to a lipid amine group through a carbodiimide coupling reagent conventionally. The ester linked compound can be prepared, for example, by coupling a lipid acid, such as phosphatidic acid, to the terminal alcohol group of a polyalkylether, using alcohol via an anhydride coupling agent. Alternatively, a short linkage fragment containing an internal ester bond and suitable end groups, such as primary amine groups, can be used to couple the polyalkylether to the amphipathic lipid through amide or carbamate linkages. Similarly, the linkage fragment may contain an internal disulfide linkage, for use in forming the compound shown at C in FIG. 5.

II. PREPARATION OF LIPOSOME COMPOSITION

The liposome composition of the invention is designed for use in delivering a drug via the bloodstream, i.e., via a parenteral route in which the liposomes are accessible to clearance mechanisms involving the reticuloendothelial system (RES). Section IIA below describes the general procedure employed for determining liposome clearance times from the bloodstream, and Section IIB, lipid component parameters which effect blood retention times, in accordance with the invention, and procedures for producing the liposome composition of the invention.

A. Measuring liposome uptake by the RES in vivo

One method used for evaluating liposome circulation time in vivo measures the distribution of intravenously injected liposomes in the bloodstream and the primary organs of the RES at selected times after injection. In the standardized model which is used, RES uptake is measured by the ratio of total liposomes in the bloodstream to total liposomes in the liver and spleen, the principal organs of the RES. In practice, age and sex matched mice are injected intravenously (IV) through the tail vein with a radiolabeled liposome composition, and each time point is determined by measuring total blood and combined liver and spleen radiolabel counts. Experimental methods are detailed in Example 5.

Since the liver and spleen account for nearly 100% of the initial uptake of liposomes by the RES, the blood/RES ratio just described provides a good approximation of the extent of uptake from the blood to the RES in vivo. For example, a ratio of about 1 or greater indicates a predominance of injected liposomes remaining in the bloodstream, and a ratio below about 1, a predominance of liposomes in the RES. For most of the lipid compositions of interest, blood/RES ratios were determined at selected intervals intervals of between 15 minutes and 24 hours. A related method which is also used herein measures blood circulation lifetime, as determined from the decrease in percent dose in the bloodstream over time.

The data obtained with the model animal system can be reasonably extrapolated to humans and veterinary animals of interest. This is because, as mentioned above, uptake of liposomes by liver and spleen has been found to occur at similar rates in several mammalian species, including mouse, rat monkey, and human (Gregoriadis, 1974; Jonah; Kimelberg, 1976; Juliano; Richardson; Lopez-Berestein). This result likely reflects the fact that the biochemical factors which appear to be most important in liposome uptake by the RES—including opsinization by serum lipoproteins, size-dependent uptake effects, and cell shielding by surface moieties—are common features of all mammalian species which have been examined.

B. Lipid Components

The lipid components used in forming the liposomes of the invention may be selected from a variety of vesicle-forming lipids, typically including phospholipids and sterols. According to one important aspect of the invention, it has been discovered that the lipids making up the bulk of the vesicle-forming lipids in the liposomes may be either fluidic lipids, e.g., phospholipids whose acyl chains are relatively unsaturated, or more rigidifying membrane lipids, such as highly saturated phospholipids. This feature of the invention is seen in Example 6, which examines blood/RES ratios in liposomes formed with PEG-PE, cholesterol, and PC having varying degrees of saturation. As seen from the data in Table 4 in Example 6, high blood/RES ratios were achieved in substantially all of the liposome formulations, independent of the extent of lipid unsaturation in the bulk PC phospholipid, and no systematic trend, as a function of degree of lipid saturation, was observed.

Accordingly, the vesicle-forming lipids may be selected to achieve a selected degree of fluidity or rigidity, to control the stability of the liposomes in serum and the rate of release of entrapped drug from the liposomes in the bloodstream. The vesicle-forming lipids may also be selected, in lipid saturation characteristics, to achieve desired liposome preparation properties. It is generally the case, for example, that more fluidic lipids are easier to formulate and size by extrusion than more rigid lipid components, and can be readily formulated in sizes down to 0.05 microns.

Similarly, it has been found that the percentage of cholesterol in the liposomes may be varied over a wide range without significant effect on observed blood circulation lifetime. The studies presented in Example 7A show virtually no change in blood circulation lifetime in the range of cholesterol between 0-30 mole percent.

It has also been found, in accordance with the invention that blood circulation lifetime is also relatively unaffected by the percentage of charged lipid components, such as phosphatidylglycerol (PG). This can be seen from FIG. 6, which plots percent loss of encapsulated marker for PEG-PE liposomes containing either 4.7 mole percent PG (triangles) or 14 mole percent PG (circles). Virtually no difference in liposome retention in the bloodstream over a 24 hour period was observed. It is noted here that the PEG-PE lipid is itself negatively charged and thus the PG represents additional negative charge on the liposome surface.

Thus, according to one feature of the invention, total liposome charge may be varied to modulate liposome stability, to achieve desired interactions with or binding to drugs. The concentration of charged lipid may be about percent or higher.

As an example, in preparing liposomes containing entrapped doxorubicin or epirubicin, additional charged lipid components may be added to increase the amount of entrapped drug, in a lipid-film hydration method of forming liposomes.

The polyalkylether lipid employed in the liposome composition is present in an amount preferably between about 1-20 mole percent, on the basis of moles of derivatized lipid as a percentage of toal total moles of vesicle-forming lipids. As noted above, the polyalkylether moiety of the lipid preferably has a molecular weight between about 120-20,000 daltons, and more preferably between about 1,000-5,000 daltons. Example 7B, which examines the effect of very short ethoxy ether moieties (120 daltons) on blood circulation lifetime ratios indicates that polyether moieties of at least about 5 carbon atoms are required to achieve significant enhancement of blood/RES ratios.

C. Preparing the Liposome Composition

The liposomes may be prepared by a variety of techniques, such as those detailed in Szoka et al, 1980. One preferred method for preparing drug-containing liposomes is the reverse phase evaporation method described by Szoka et al and in U.S. Pat. No. 4,235,871. In this method, a solution of liposome-forming lipids is mixed with a smaller volume of an aqueous medium, and the mixture is dispersed to form a water-in-oil emulsion, preferably using pyrogen-free components. The drug or other pharmaceutical agent to be delivered is added either to the lipid solution, in the case of a lipophilic drug, or to the aqueous medium, in the case of a water-soluble drug.

After removing the lipid solvent by evaporation, the resulting gel is converted to liposomes, with an encapsulation efficiency, for a water-soluble drug, of up to 50%. The reverse phase evaporation vesicles (REVs) have typical average sizes between about 2-4 microns and are predominantly oligolamellar, that is, contain one or a few lipid bilayer shells. The REVs may be readily sized, as discussed below, by extrusion to give oligolamellar vesicles having a maximum selected size preferably between about 0.05 to 0.5 microns.

To form MLV's, a mixture of liposome-forming lipids of the type detailed above dissolved in a suitable solvent is evaporated in a vessel to form a thin film, which is then covered by an aqueous medium. The lipid film hydrates to form MLVs, typically with sizes between about 0.1 to 10 microns. These vesicles, when unsized, show relatively poor blood/RES ratios, as seen in Table 9, for the unextruded MLV composition. Typically, MLVs are sized down to a desired size range of 0.5 or less, and preferably between about 0.05 and 0.2 microns by extrusion.

One effective sizing method for REVs and MLVs involves extruding an aqueous suspension of the liposomes through a polycarbonate membrane having a selected uniform pore size, typically 0.05, 0.08, 0.1, 0.2, or 0.4 microns (Szoka). The pore size of the membrane corresponds roughly to the largest sizes of liposomes produced by extrusion through that membrane, particularly where the preparation is extruded two or more times through the same membrane. This method of liposome sizing is used in preparing homogeneous-size REV and MLV compositions described in Examples 4A and 4B below. A more recent method involves extrusion through an asymmetric ceramic filter. The method is detailed in U.S. patent application for Liposome Extrusion Method, Ser. No. 829,710, filed Feb. 13, 1986.

Alternatively, the REV or MLV preparations can be treated to produce small unilamellar vesicles (SUVs) which are characterized by sizes in the 0.04–0.08 micron range. SUVs may be useful, for example, in targeting a tumor tissue which permits selective passage of small particles, typically than about 0.1 micron, through the capillary walls supplying the tumor. As noted above, SUVs may be formed readily from fluid vesicle-forming lipids.

After final sizing, the liposomes can be treated, if necessary, to remove free (non-entrapped) drug. Conventional separation techniques, such as centrifugation, diafiltration, and molecular-sieve chromatography are suitable. The composition can be sterilized by filtration through a conventional 0.45 micron depth filter.

III. UTILITY

The significantly increased circulation half life of liposomes constructed as above can be exploited in several types of therapeutic applications. In one application, the liposome composition is designed for sustained release of a liposome-associated drug into the bloodstream by long-life circulating liposomes. As seen above, liposomes constructed according to the invention can be maintained predominantly in the bloodstream up to 24 hours, and therefore sustained released of the drug at physiologically effective levels for up to about 1 day or more can be achieved. As noted above, the liposomes can be prepared from vesicle-forming lipids having a wide range of rigidifying properties, to achieve selected liposome stability and drug release rates from the liposomes in the bloodstream.

A variety of drugs or other pharmacologically active agents are suitable for delivery by the liposome composition. One general class of drugs include water-soluble, liposome-permeable compounds which are characterized by a tendency to partition preferentially into the aqueous compartments of the liposome suspension, and to equilibrate, over time, between the inner liposomal spaces and outer bulk phase of the suspension. Representative drugs in this class include terbutaline, albuterol, atropine methyl nitrate, cromolyn sodium, propranalol, flunoisolide, ibuprofin, gentamycin, tobermycin, pentamidine, penicillin, theophylline, bleomycin, etoposide, captoprel, n-acetyl cysteine, verapamil, vitamins, and radio-opaque and particle-emitter agents, such as chelated metals. Because of the tendency of these agents to equilibrate with the aqueous composition of the medium, it is preferred to store the liposome composition in lyophilized form, with rehydration shortly before administration. Alternatively, the composition may be prepared in concentrated form, and diluted shortly before administration. The latter approach is detailed in U.S. patent application for "Liposome Concentrate and Method", Ser. No. 860,528, filed May 7, 1986.

A second general class of drugs are those which are water-soluble, but liposome-impermeable. For the most part, these are peptide or protein molecules, such as peptide hormones, enzymes, enzyme inhibitors, apolipoproteins, and higher molecular weight carbohydrates characterized by long-term stability of encapsulation. Representative compounds in this class include calcitonin, atriopeptin, $\alpha$-1 antitrypsin (protease inhibitor), interferon, oxytocin, vasopressin, insulin, interleukin-2, superoxide dismutase, tissue plasminogen activator (TPA), plasma factor 8, epidermal growth factor, tumor necrosis factor, lung surfactant protein, interferon, lipocortin, $\alpha$-interferon, macrophage colony stimulating factor, and erythropoietin.

A third class of drugs are lipophilic molecules which tend to partition into the lipid bilayer phase of the liposomes, and which are therefore associated with the liposomes predominantly in a membrane-entrapped form. The drugs in this class are defined by an oil/water partition coefficient, as measured in a standard oil/water mixture such as octanol/water, of greater than 1 and preferably greater than about 5. Representative drugs include prostaglandins, amphotericin B, progesterone, isosorbide dinitrate, testosterone, nitroglycerin, estradiol, doxorubicin, epirubicin, beclomethasone and esters, vitamin E, cortisone, dexamethasone and esters, and betamethasone valerete.

For sustained drug-release via the bloodstream, the liposome composition is administered intravenously in an amount which provides a suitable drug dosage over the expected delivery time, typically 12–24 hours. The injection may be given as a single bolus or slowly by i.v. drip, to allow gradual dispersal of the liposomes from the site of injection.

In another application, the liposome composition is designed for targeting to a specific target tissue or organ. The extended lifetime of the liposomes in the bloodstream makes it possible for a significant fraction of the injected liposomes to reach the target site before being removed from the bloodstream by the RES. For example, this feature allows for targeting a tumor tissue, for drug treatment by intravenous administration to a tumor-bearing subject. For targeting to a tumor site, the liposomes may be prepared as SUVs, for extravisation into the tumor site through capillaries supplying the tumor.

As another example, the liposomes may be prepared with surface-bound ligand molecules, such as antibodis, which are effective to bind specifically and with high affinity to ligand-binding molecules, such as antigens, which are localized specifically on target cells. As an example, the ligand molecules may be tumor-specific antibodies, for binding to tumor-specific antigens on tumor cells. As another example, the ligand may be a CD4 peptide, effective to bind specifically to HIV-infected T cells.

A variety of methods for coupling ligands to the surface of liposomes are known, including incorporation of ligand-derivatized lipid components into liposomes or coupling of ligands to activated liposome surface components.

The targeted liposomes may be prepared to include cancer chemotherapeutic agents, such as those listed above. In one preferred embodiment, the liposomes are prepared to include PEG-PE and PG, to a final concentration of charged lipids up to 40 mole percent, doxorubicin, and remainder neutral phospholipids or neutral phospholipids and cholesterol.

In a liposome composition which is useful for radioimaging of solid tumor regions, the liposomes are prepared with encapsulated radio-opaque or particle-emission metal, typically in a chelated form which substantially prevents permeation through the liposome bilayer.

In still another application, the liposome composition is designed to enhance uptake of circulating cells or other blood-borne particles, such as bacteria, virus-infected blood cells and the like. Here the long-life liposomes are prepared to include surface-bound ligand molecules, as above, which bind specifically and with high affinity to the selected blood-borne cells. Once bound to the blood-borne particles, the liposomes can enhance uptake by the RES.

Polyalkylether moieties on the liposomes may be derivatized the associated anphipathic lipid by an ester, peptide, or disulfide bond which can be cleaved, after liposome binding, to the target cell, to further enhance RES particle clearance.

Studies performed in support of the present invention indicate that the liposome composition of the invention provides an enhancement in blood circulation lifetime which is equal, and in some cases superior, to the most effective RES-evading rigid-lipid liposomes which have been reported heretofore, including liposomes containing $GM_1$, and membrane-rigidifying lipids.

The blood circulation lifetimes achieved in the present invention are substantially greater than any other fluid-lipid liposomes which were examined.

The following examples illustrate methods of preparing liposomes with enhanced circulation times, and for accessing circulation times in vivo and in vitro. The examples are intended to illustrate specific liposome compositions and methods of the invention, but are in no way intended to limit the scope thereof.

MATERIALS

Cholesterol (Chol) was obtained from Sigma (St. Louis, Mo). Sphingomyelin (SM), egg phosphatidylcholine (lecithin or PC), partially hydrogenated PC having the composition IV40, IV30, IV20, IV10, and IV1, phosphatidylglycerol (PG), phosphatidylethanolamine (PE), dipalmitoyl-phosphatidyl glycerol (DPPG), dipalmitoyl PC (DPPC), dioleyl PC (DOPC) and distearoyl PC (DSPC) were obtained from Avanti Polar Lipids (Birmingham, Ala).

[$^{125}$I]-tyraminyl-inulin was made according to published procedures. $^{67}$Gallium-8-hydroxyquinoline was supplied by NEN Neoscan (Boston, Mass).

EXAMPLE 1

Preparation of PEG-PE Linked by Cyanuric Chloride

A. Preparation of activated PEG 2-0-Methoxypolyethylene glycol 1900-4,6-dichloro-1,3,5 triazine previously called activated PEG was prepared as described in *J. Biol. Chem.*, 252:3582 (1977) with the following modifications.

Cyanuric chloride (5.5 g; 0.03 mol) was dissolved in 400 ml of anhydrous benzene containing 10 g of anhydrous sodium carbonate, and PEG-1900 (19 g; 0.01 mol) was added and the mixture was stirred overnight at room temperature. The solution was filtered, and 600 ml of petroleum ether (boiling range, 35°-60°) was added slowly with stirring. The finely divided precipitate was collected on a filter and redissolved in 400 ml of benzene. The precipitation and filtration process was repeated several times until the petroleum ether was free of residual cyanuric chloride as determined by high pressure liquid chromatography on a column (250×3.2 mm) of 5-m "LiChrosorb" (E. Merck), developed with hexane, and detected with an ultraviolet detector. Titration of activated PEG-1900 with silver nitrate after overnight hydrolysis in aqueous buffer at pH 10.0, room temperature, gave a value of 1.7 mol of chloride liberated/mol of PEG.

TLC analysis of the product was effected with TLC reversed-phase plates obtained from Baker using methanol-water, 4:1; v/v, as developer and exposure to iodine vapor for visualization. Under these conditions, the starting methoxy polyglycol 1900 appeared at $R_f=0.54$ to 0.60. The activated PEG appeared at $R_f=0.41$. Unreacted cyanuric chloride appeared at $R_f=0.88$ and was removed.

The activated PEG was analyzed for nitrogen and an appropriate correction was applied in selecting the quantity of reactant to use in further synthetic steps. Thus, when the product contained only 20% of the theoretical amount of nitrogen, the quantity of material used in the next synthetic step was increased by 100/20, or 5-fold. When the product contained 50% of the theoretical amount of nitrogen, only 100/50 or a 2-fold increase was needed.

B. Preparation of N-(4-Chloro-polyglycol 1900)-1,3,5-triazinyl egg phosphatidylethanolamine.

In a screw-capped test tube, 0.74 ml of a 100 mg/ml (0.100 mmole) stock solution of egg phosphatidylethanolamine in chloroform was evaporated to dryness under a stream of nitrogen and was added to the residue of the activated PEG described in section A, in the amount to provide 205 mg (0.100 mmole). To this mixture, 5 ml anhydrous dimethyl formamide was added. 27 microliters (0.200 mmole) triethylamine was added to the mixture, and the air was displaced with nitrogen gas. The mixture was heated overnight in a sand bath maintained at 110° C.

The mixture was then evaporated to dryness under vacuum and a pasty mass of crystalline solid was obtained. This solid was dissolved in 5 ml of a mixture of 4 volumes of acetone and 1 volume of acetic acid. The resulting mixture was placed at the top of a 21 mm×240 mm chromatographic absorption column packed with silica gel (Merck Kieselgel 60, 70–230 mesh) which had first been moistened with a solvent composed of acetone acetic acid, 80/20; v/v.

The column chromatography was developed with the same solvent mixture, and separate 20 to 50 ml aliquots of effluent were collected. Each portion of effluent was assayed by TLC on silica gel coated plates, using 2-butanone/acetic acid/water; 40/25/5; v/v/v as developer and iodine vapor exposure for visualization. Fractions containing only material of $R_f=$ about 0.79 were combined and evaporated to dryness under vacuum. Drying to constant weight under high vacuum afforded 86 mg (31.2 micromoles) of nearly colorless solid N-(4-chloro-polyglycol 1900)-1,3,5-triazinyl egg phosphatidylethanolamine containing phosphorous.

The solid compound was taken up in 24 ml of ethanol/-chloroform; 50/50 chloroform and centrifuged to remove insoluble material. Evaporation of the clarified solution to dryness under vacuum afforded 21 mg (7.62 micromoles) of colorless solid.

EXAMPLE 2 Preparation of the Carbamate-Linked PEG-PE

A. Preparation of the imidazole carbamate of polyethylene glycol methyl ether 1900.

9.5 grams (5 mmoles) of polyethylene glycol methyl ether 1900 obtained from Aldrich Chemical Co. was dissolved in 45 ml benzene which has been dried over molecular sieves. 0.89 grams (5.5 mmoles) of pure carbonyl diimidazole was added. The purity was checked by an infra-red spectrum. The air in the reaction vessel was displaced with nitrogen. Vessel was enclosed and heated in a sand bath at 75° C. for 16 hours.

The reaction mixture was cooled and the clear solution formed at room temperature. The solution was diluted to 50.0 ml with dry benzene and stored in the refrigerator as a 100 micromole/ml stock solution of the imidazole carbamate of PEG ether 1900.

B. Preparation of the phosphatidylethanolamine carbamate of polyethylene glycol methyl ether 1900.

10.0 ml (1 mmol) of the 100 mmol/ml stock solution of the imidazole carbamate of polyethylene glycol methyl ether 1900 (compound X) was pipetted into a 10 ml pear-shaped flask. The solvent was removed under vacuum. 3.7 ml of a 100 mg/ml solution of egg phosphatidyl ethanolamine (V) in chloroform (0.5 mmol) was added. The solvent was evaporated under vacuum. 2 ml of 1,1,2,2-tetrachloroethylene and 139 microliters (1.0 mmol) of triethylamine VI was added. The vessel was closed and heated in a sand bath maintained at 95° C. for 6 hours. At this time, thin-layer chromatography was performed with fractions of the above mixture to determine an extent of conjugation on SiO2 coated TLC plates, using butanone/acetic acid/water; 40/5/5; v/v/v; was performed as developer. I2 vapor visualization revealed that most of the free phosphatidyl ethanolamine of Rf=0.68, had reacted, and was replaced by a phosphorous-containing lipid at $R_f$=0.78 to 0.80.

The solvent from the remaining reaction mixture was evaporated under vacuum. The residue was taken up in 10 ml methylene chloride and placed at the top of a 21 mm×270 mm chromatographic absorption column packed with Merck Kiesel-gel 60 (70–230 mesh silica gel), which has been first rinsed with methylene chloride. The mixture was passed through the column, in sequence, using the following solvents.

TABLE 1

| ml | Volume % of Methylene Chloride | Volume % Methanol With 2% Acetic Acid |
|---|---|---|
| 100 | 100% | 0% |
| 200 | 95% | 5% |
| 200 | 90% | 10% |
| 200 | 85% | 15% |
| 200 | 60% | 40% |

50 ml portions of effluent were collected and each portion was assayed by TLC on SiO2 - coated plates, using I2 vapor absorption for visualization after development with chloroform/methanol/water/concentrated ammonium hydroxide; 130/70/8/0.5%; v/v/v/v. Most of the phosphates were found in fractions 11, 12, 13 and 14.

These fractions were combined, evaporated to dryness under vacuum and dried in high vacuum to constant weight. They yielded 669 mg of colorless wax of phosphatidyl ethanolamine carbamate of polyethylene glycol methyl ether. This represented 263 micromoles and a yield of 52.6% based on the phosphatidyl ethanolamine.

An NMR spectrum of the product dissolved in deutero-chloroform showed peaks corresponding to the spectrum for egg PE, together with a strong singlet due to the methylene groups of the ethylene oxide chain at Delta=3.4 ppm. The ratio of methylene protons from the ethylene oxide to the terminal methyl protons of the PE acyl groups was large enough to confirm a molecular weight of about 2000 for the polyethylene oxide portion of the molecule of the desired product polyethylene glycol conjugated phosphatidyethanolamine carbamate, M. W. 2,654.

EXAMPLE 3 Preparation of Ethylene-Linked PEG-PE

A. Preparation of I-trimethylsilyloxy-polyethylene glycol is illustrated in Reaction Scheme 3A.

15.0 gm (10 mmoles) of polyethylene glycol) M.Wt. 1500, (Aldrich Chemical) was dissolved in 80 ml benzene. 1.40 ml (11 mmoles) of chlorotrimethyl silane (Aldrich Chemical Co.) and 1.53 ml (1 mmoles) of triethylamine was added. The mixture was stirred at room temperature under an inert atmosphere for 5 hours.

The mixture was filtered with suction to separate crystals of triethylammonium chloride and the crystals were washed with 5 ml benzene. Filtrate and benzene wash liquids were combined. This solution was evaporated to dryness under vacuum to provide 15.83 grams of colorless oil which solidified on standing.

TLC of the product on Si-$C_{18}$ reversed-phase plates using a mixture of 4 volumes of ethanol with 1 volume of water as developer, and iodine vapor visalization, revealed that all the polyglycol 1500 ($R_f$=0.93) has been consumed, and was replaced by a material of $R_f$=0.82. An infra-red spectrum revealed absorption peaks characteristic only of polyglycols.

Yield of I-trimethylsilyoxypolyethylene glycol, M. W. 1500 was nearly quantitative.

B. Preparation of trifluoromethane sulfonyl ester of I-trimethylsilyloxy-polyethylene glycol.

15.74 grams (10 mmol) of the crystalline I-trimethylsilyloxy polyethylene glycol obtained above was dissolved in 40 ml anhydrous benzene and cooled in a bath of crushed ice. 1.53 ml (11 mmol) triethylamine and 1.85 ml (11 mmol) of trifluoromethanesulfonic anhydride obtained from Aldrich Chemical Co. were added and the mixture was stirred over night under an inert atmosphere until the reaction mixture changed to a brown color.

The solvent was then evaporated under reduced pressure and the residual syrupy paste was diluted to 100.0 ml with methylene chloride. Because of the great reactivity of trifluoromethane sulfonic esters, no further purification of the trifluoromethane sulfonyl ester of I-trimethylsilyloxy polyethylene glycol was done.

C. Preparation of N-1-trimethylsilyloxy polyethylene glycol 1500 PE. 10 ml of the methylene chloride stock solution of the trifluoromethane sulfonyl ester of 1-trimethylsilyloxy polyethylene glycol was evaporated to dryness under vacuum to obtain about 1.2 grams of residue (approximately 0.7 mmoles). To this residue, 3.72 ml of a chloroform solution containing 372 mg (0.5 mmoles) egg PE was added. To the resulting solution, 139 microliters (1.0 mmole) of triethylamine was added and thessolvent was evaporated under vacuum. To the obtained residue, 5 ml dry dimethyl formamide and 70 microliters (0.50 mmoles) triethylamine (VI) was added. Air from the reaction vessel was displaced with nitrogen. The vessel was closed and heated in a sand bath a 110° C. for 22 hours. The solvent was evaporated under vacuum to obtain 1.58 grams of brownish colored oil. A 21×260 mm chromatographic absorption column filled with Kieselgel 60 silica 70-230 mesh, was prepared and rinsed with a solvent composed of 40 volumes of butanone, 25 volumes acetic acid and 5 volumes of water. The crude product was dissolved in 3 ml of the same solvent and transferred to the top of the chromatography column. The chromatogram was developed with the same solvent and sequential 30 ml portions of effluent were assayed each by TLC.

The TLC assay system used silica gel coated glass plates, with solvent combination butanone/acetic acid/water; 40/25/5; v/v/v. Iodine vapor absorption served for visualization. In this solvent system, the N-1-trimethylsilyloxy polyethylene glycol 1500 PE appeared at $R_f=0.78$. Unchanged PE appeared at $R_f=0.68$.

The desired N-1-trimethylsilyloxy polyethylene glycol 1500 PE was a chief constituent of the 170-300 ml portions of column effluent. When evaporated to dryness under vacuum these portions afforded 111 mg of pale yellow oil of compound.

D. Preparation of N-polyethylene glycyl 1500: phosphatidyl-ethanolamine acetic acid deprotection.

Once-chromatographed, PE compound was dissolved in 2 ml of tetrahydrofuran. To this, 6 ml acetic acid and 2 ml water was added. The resulting solution was let to stand for 3 days at 23° C. The solvent from the reaction mixture was evaporated under vacuum and dried to constant weight to obtain 75 mg of pale yellow wax. TLC on Si-C18 reversed-phase plates, developed with a mixtrue of 4 volumes ethanol, 1 volume water, indicated that some free PE and some polyglycol-like material formed during the hydrolysis.

The residue was dissolved in 0.5 ml tetrahydrofuran and diluted with 3 ml of a solution of ethanol water; 80:20; v:v. The mixture was applied to the top of a 10 mm×250 mm chromatographic absorption column packed with octadecyl bonded phase silica gel and column was developed with ethanol water 80:20% by volume, collecting sequential 20 ml portions of effluent. The effluent was assayed by reversed phase TLC. Fractions containing only product of Rf=0.08 to 0.15 were combined. This was typically the 20-100 ml portion of effluent. When evaporated to dryness, under vacuum, these portions afforded 33 mg of colorless wax PEG-PE corresponding to a yield of only 3%, based on the starting phosphatidyl ethanolamine.

NMR analysis indicated that the product incorporated both PE residues and polyethylene glycol residues, but that in spite of the favorable-appearing elemental analysis, the chain length of the polyglycol chain has been reduced to about three to four ethylene oxide residues. The product prepared was used for a preparation of PEG-PE liposomes.

E. Preparation of N-Polyethylene glycol 1500 P. E. by fluoride deprotection.

500 mg of crude N-1-trimethylsilyloxy polyethylene glycol PE was dissolved in 5 ml tetrahydrofuran and 189 mg (0.600 millimoles) of tetrabutyl ammonium fluoride was added and agitated until dissolved. The reactants were let to stand over night at room temperature (20° C.).

The solvent was evaporated under reduced pressure and the residue was dissolved in 10 ml chloroform, washed with two successive 10 ml portions of water, and centrifuged to separate chloroform and water phases. The chloroform phase was evaporated under vacuum to obtain 390 mg of orange-brown wax, which was determined to be impure N-polyethylene glycol 1500 PE compound.

The wax was re-dissolved in 5 ml chloroform and transferred to the top of a 21×270 mm column of silica gel moistened with chloroform. The column was developed by passing 100 ml of solvent through the column the following solvents in sequence were used.

TABLE 2

| Volume % Chloroform | Volume % Methanol Containing 2% Conc. Ammonium Hydroxide/methanol |
|---|---|
| 100% | 0% |
| 95% | 5% |
| 90% | 10% |
| 85% | 15% |
| 80% | 20% |
| 70% | 30% |
| 60% | 40% |
| 50% | 50% |
| 0% | 100% |

Separated 50 ml fractions of column effluent were saved. The fractions of the column were separated by TLC on Si-C18 reversed-phase plates. TLC plates were developed with 4 volumes of ethanol mixed with 1 volume of water. Visualization was done by exposure to iodine vapor.

Only those fractions containing an iodine-absorbing lipid of $R_f$ about 0.20 were combined and evaporated to dryness under vacuum and dried in high vacuum to constant weight. In this way 94 mg of waxy crystalline solid was obtained of M. W. 2226. The proton NMR spectrum of this material dissolved in deuterochloroform showed the expected peaks due to the phosphatidyl ethanolamine portion of the molecule, together with a few methylene protons attributable to polyethylene glycol. (Delta=3.7).

EXAMPLE 4 Preparation of REVs and MLVs

A. Sized REVs

A total of 15 μmoles of the selected lipid components, in the mole ratios indicated in the examples below, were dissolved in chloroform and dried as a thin film by rotary evaporation. This lipid film was dissolved in 1 ml of diethyl ether washed with distilled water. To this lipid solution was added 0.34 ml of an aqueous buffer solution containing 5 mM Tris, 100 mM NaCl, 0.1 mM EDTA, pH 7.4, and the mixture was emulsified by sonication for 1 minute, maintaining the temperature of the solution at or below room temperature. Where the liposomes were prepared to contain encapsulated [125I] tyraminyl-inulin, such was included in the phosphate buffer at a concentration of about 4 μCi/ml buffer.

The ether solvent was removed under reduced pressure at room temperature, and the resulting gel was taken up in 0.1 ml of the above buffer, and shaken vigorously. The resulting REV suspension had particle sizes, as determined by microscopic examination, of between about 0.1 to 20 microns, and was composed predominantly of relatively large (greater than 1 micron) vesicles having one or only a few bilayer lamellae.

The liposomes were extruded twice through a polycarbonate filter (Szoka, 1978), having a selected pore size of 0.4 microns or 0.2 microns. Liposomes extruded through the 0.4 micron filter averaged 0.17± (0.05) micron diameters, and through the 0.2 micron filter, 0.16 (0.05) micron diameters. Non-encapsulated [125I] tyraminyl-inulin was removed by passing the extruded liposomes through Sephadex G-50 (Pharmacia).

B. Sized MLVs

Multilamellar vesicle (MLV) liposomes were prepared according to standard procedures by dissolving a mixture of lipids in an organic solvent containing primarily $CHCl_3$ and drying the lipids as a thin film by rotation under reduced pressure. In some cases a radioactive label for the lipid phase was added to the lipid solution before drying. The lipid film was hydrated by addition of the desired aqueous phase and 3 mm glass beads followed by agitation with a vortex and shaking above the phase transition temperature of the phospholipid component for at least 1 hour. In some cases a radioactive label for the aqueous phase was included in the buffer. In some cases the hydrated lipid was repeatedly frozen and thawed three times to provide for ease of the following extrusion step.

The size of the liposome samples was controlled by extrusion through defined pore polycarbonate filters using pressurized nitrogen gas. In one procedure, the liposomes were extruded one time through a filter with pores of 0.4 μm and then ten times through a filter with pores of 0.1 μm. In another procedure, the liposomes were extruded three times through a filter with 0.2 μm pores followed by repeated extrusion with 0.05 μm pores until the mean diameter of the particles was below 100 nm as determined by DLS. Unencapsulated aqueous components were removed by passing the extruded sample through a gel permeation column separating the liposomes in the void volume from the small molecules in the included volume.

C. Loading $^{67}Ga$ Into DF-Containing Liposomes

The protocol for preparation of $Ga^{67}$-DF labeled liposomes as adapted from known procedures (Gabizon). Briefly, liposomes were prepared with the ion chelator desferal mesylate encapsulated in the internal aqueous phase to bind irreversibly Ga transported through the bilayer by hydroxyquinoline (oxine).

D. Dynamic Light Scattering

Liposome particle size distribution measurements were obtained by DLS using a NICOMP Model 200 with a Brookhaven Instruments BI-2030AT autocorrelator attached. The instruments were operated according to the manufacturer's instructions. The NICOMP results were expressed as the mean diameter and standard deviation of a Gaussian distribution of vesicles by relative volume.

EXAMPLE 5

Kinetics of Liposome Clearance from the Bloodstream

A. Measuring Blood Circulation Time and Blood/RES Ratios

In vivo studies of liposomes were performed in two different animal models: Swiss-Webster mice at 25 g each and laboratory rats at 200–300 g each. The studies in mice involved tail vein injection of liposome samples at 1 μM phospholipid/mouse followed by animal sacrifice after a defined time and tissue removal for label quantitation by gamma counting. The weight and percent of the injected dose in each tissue were determined. The studies in rats involved establishment of a chronic catheter in a femoral vein for removal of blood samples at defined times after injection of liposome samples in a catheter in the other femoral artery at 3–4 μM phospholipid/rat. The percent of the injected dose remaining in the blood at several time points up to 24 hours was determined.

B. Time Course of Liposome Retention in the Bloodstream

PEG-PE composed of methoxy PEG, molecular weight 1900 and 1-palmitoyl-2-oleyl-PE (POPE) was prepared as in Example 2. The PEG-POPE lipid was combined with and partially hydrogenated egg PC (PHEPC) in a lipid:lipid mole ratio of about 0.1:2, and the lipid mixture was hydrated and extruded through a 0.1 micron polycarbonate membrane, as described in Example 4, to produce MLV's with average size about 0.1 micron. The MLV lipids included a small amount of radio-labeled lipid marker $^{14}C$-cholesteryl oleate, and the encapsulated marker $^3H$-inulin.

Figure 7:
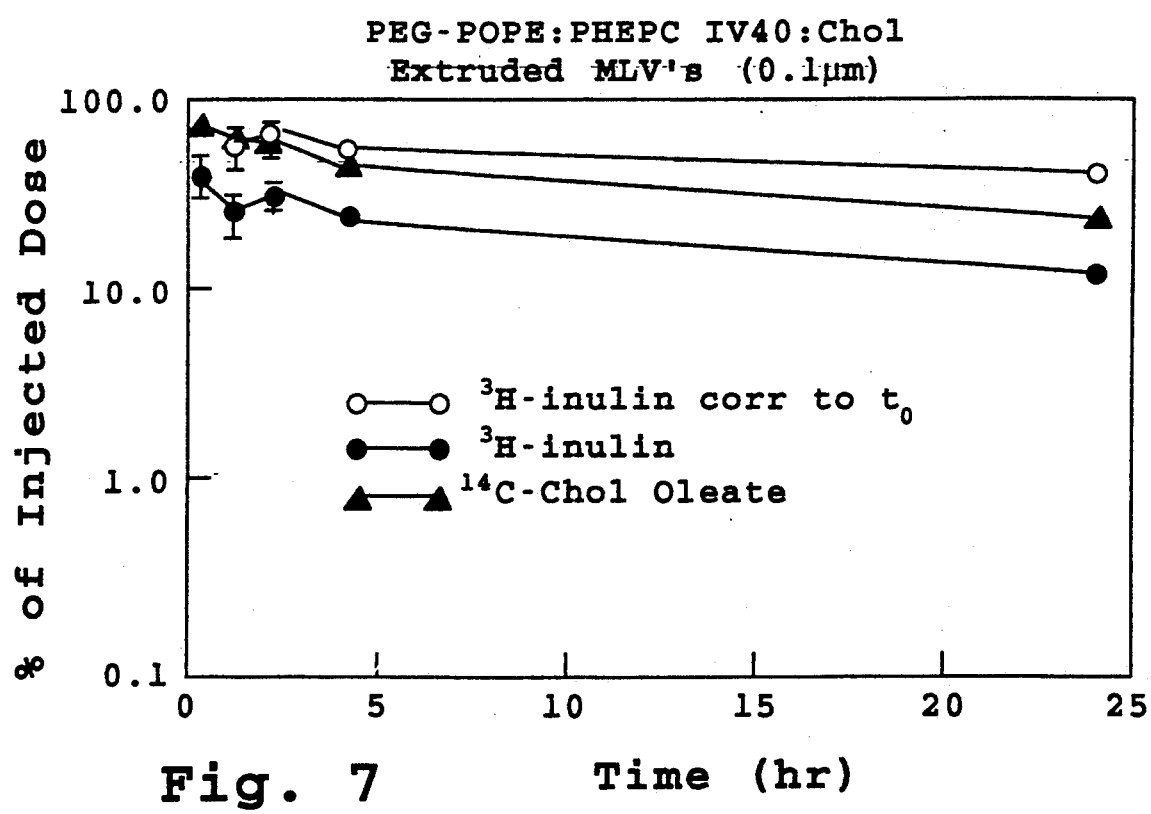
FIG. 7 is a plot similar to that of FIG. 6, showing retention time in liposomes composed of predominantly unsaturated phospholipid components.

The liposome composition was injected and the percent initial injected dose in mice was determined as described in Example 4, at 1, 2, 3, 4, and 24 after injection. The time course of loss of radiolabeled material is seen in FIG. 7 which is a plot of percent injected dose for encapsulated inulin (solid circles), inulin marker corrected to the initial injection point of 100% (open circles), and lipid marker (closed triangles), over a 24-hour period post injection. As seen, both lipid and encapsulated markers showed greater than 10% of original injected dose after 24 hours.

EXAMPLE 6

Effect of Phospholipid Acyl-Chain Saturation on Blood/RES Ratios in PEG-PE Liposomes PEG-PE composed of methoxy PEG, molecular weight 1900 and distearylPE (DSPE) was prepared as in Example 2. The PEG-PE lipids were formulated with selected lipids from among sphingomyelin (SM), fully hydrogenated soy PC (PC), cholesterol (Chol), partially hydrogenated soy PC (PHSPC), and partially hydrogenated PC lipids identified as PC IV1, IV10, IV20, IV30, and IV40 in Table 3. The lipid components were mixed in the molar ratios shown at the left in Table 4, and used to form MLV's sized to 0.1 micron as described in Example 4.

TABLE 3

| Egg PC Form | Phase Transition Temp.(°C.) Range | Phase Transition Temp.(°C.) Midpoint | Mole % Fatty Acid Comp. 18:0 | 18:1 | 18:2 | 20:0 | 20:1-4 | 22:0 | 22:1-6 |
|---|---|---|---|---|---|---|---|---|---|
| Native | <20 | | 12 | 30 | 15 | 0 | 3 | 0 | 5 |
| IV 40 | | <20 | 14 | 32 | 4 | 0 | 3 | 0 | 4 |
| IV 30 | <20–30 | | 20 | 22 | 0 | 1 | 2 | 1 | 3 |
| IV 20 | 23–45 | 41 | 30 | 10 | 0 | 2 | 1 | 2 | 3 |

TABLE 3-continued

| Egg PC Form | Phase Transition Temp.(°C.) | | Mole % Fatty Acid Comp. | | | | | |
|---|---|---|---|---|---|---|---|---|
| | Range | Midpoint | 18:0 | 18:1 | 18:2 | 20:0 | 20:1-4 | 22:0 | 22:1-6 |
| IV 10 | 37-50 | 46 | 42 | 4 | 0 | 3 | 1 | 4 | 2 |
| IV 1 | 49-54 | 52 | 56 | 0 | 0 | 5 | 0 | 6 | 0 |

TABLE 4

| | Blood | L + S (RES) | B/RES | % Rec |
|---|---|---|---|---|
| PEG-PE:SM:PC:Chol 0.2:1:1:1 | 19.23 | 6.58 | 2.92 | 49.23 |
| PEG-PE:PHSPC:Chol 0.15:1.85:1 | 20.54 | 7.17 | 2.86 | 55.14 |
| PEG-PE:PC IV1:Chol 0.15:1.85:1 | 17.24 | 13.71 | 1.26 | 60.44 |
| PEG-PE:PC IV1:Chol (Two animals) 0.15:1.85:1 | 19.16 | 10.07 | 1.90 | 61.87 |
| PEG-PE:PC IV10:Chol (Two animals) 0.15:1.85:1 | 12.19 | 7.31 | 1.67 | 40.73 |
| PEG-PE:PC IV10:Chol 0.15:1.85:1 | 2.4 | 3.5 | 0.69 | 12.85 |
| PEG-PE:PC IV20:Chol 0.15:1.85:1 | 24.56 | 7.52 | 3.27 | 62.75 |
| PEG-PE:PC IV20:Chol 0.15:1.85:1 | 5.2 | 5.7 | 0.91 | 22.1 |
| PEG-PE:PC IV40:Chol 0.15:1.85:1 | 19.44 | 8.87 | 2.19 | 53.88 |
| PEG-PE:PC IV40:Chol 0.15:1.85:1 | 17.2 | 9.35 | 1.84 | 58.09 |
| PEG-PE:PC IV40:Chol 0.15:1.85:0.5 | 20.3 | 8.8 | 2.31 | 45.5 |
| PEG-PE:EPC:Chol 0.15:1.85:1 | 15.3 | 9.6 | 1.59 | 45.9 |

24 hours after injection, the percent material injected (as measured by percent of [57]Ga-desferal) remaining the blood and in the liver (L) and spleen (S) were determined, and these values are shown in the two data columns at the left in Table 4. The blood and L+S (RES) values were used to calculate a blood/RES value for each composition. The column at the right in Table 4 shows total amount of radioactivity recovered. The two low total recovery values in the table indicate anomolous clearance behavior.

The results from the table demonstrate that the blood/RES ratios are largely independent of the fluidity, or degree of saturation of the phospholipid components forming the liposomes. In particular, there was no systematic change in blood/RES ratio observed among liposomes containing largely saturated PC components (e.g., IV1 and IV10 PC's), largely unsaturated PC components (IV40), and intermediate-saturation components (e.g., IV20).

In addition, a comparison of blood/RES ratios obtained using the relatively saturated PEG-DSPE compound and the relatively unsaturated PEG-POPE compound (Example 5) indicates that the degree of saturation of the derivatized lipid is itself not critical to the ability of the liposomes to evade uptake by the RES.

EXAMPLE 7

Effect of Cholesterol and Ethoxylated Cholesterol on Blood/RES Ratios in PEG-PE Liposomes A. Effect of added cholesterol PEG-PE composed of methoxy PEG, molecular weight 1900 and was derivatized DSPE as described in Example 6. The PEG-PE lipids were formulated with selected lipids from among sphingomyelin (SM), fully hydrogenated soy PC (PC), and cholesterol (Chol), as indicated in the column at the left in Table 5 below. The three formulations shown in the table contain about 30, 15, and 0 mole percent cholesterol. Both REV's (0.3 micron size) and MLV's (0.1 micron size) were prepared, substantially as in Example 4, with encapsulated tritium-labeled inulin.

The percent encapsulated inulin remaining in the blood 2 and 24 hours after administration, given at the right in the table, show no measurable effect of cholesterol, in the range 0-30 mole percent.

TABLE 5

| | % Injected Dose In Blood | | | |
|---|---|---|---|---|
| | 2 HR. [3]H Aqueous Label (Leakage) | 24 HR. | 2 HR. [14]C - Lipid Label | 24 HR. |
| [3]H-Inulin | | | | |
| (1) SM:PC:Chol:PEG-DSPE 1:1:1:0.2 | | | | |
| 100 nm MLV | 19 | 5 | 48 | 24 |
| 300 nm REV | 23 | 15 | 67 | 20 |
| (2) SM:PC:Chol:PEG-DSPE 1:1:0.5:0.2 | 23 | 15 | 71 | 17 |
| 300 nm REV | | | | |
| (3) SM:PC:PEG-DSPE 1:1:0.2 | | | | |
| 100 nm MLV | 19 | 6 | 58 | 24 |
| 300 nm REV | 32 | 23 | 76 | 43 |

B. Effect of ethoxylated cholesterol

Methoxy-ethyoxy-cholesterol was prepared by coupling methoxy ethanol to cholesterol via the triflurosulfonate coupling method described in Section I. PEG-PE composed of methoxy PEG, molecular weight 1900 and was derivatized DSPE as described in Example 6. The PEG-PE lipids were formulated with selected lipids from among distearylPC (DSPC), partially hydrogenated soy PC (PHSPC), cholesterol, and ethoxylated cholesterol, as indicated at the right in Table 6. The data show that (a) ethoxylated cholesterol, in combination with PEG-PE, gives about the same degree of enhancement of liposome lifetime in the blood as PEG-PE alone. By itself, the ethoxylated cholesterol provides a moderate degree of enhancement of liposome lifetime, but substantially less than that provided by PEG-PE.

TABLE 6

| Formulation | % Injected Dose In Blood $^{14}$C-Chol-Oleate | |
|---|---|---|
| | 2 HR. | 24 HR. |
| HSPC:Chol:PEG-DSPE 1.85:1:0.15 | 55 | 9 |
| HSPC:Chol:PEG-DSPE:PEG$_5$-Chol 1.85:0.85:0.15:0.15 | 57 | 9 |
| HSPC:Chol:HPG:PEG$_5$-Chol 1.85:0.85:0.15:0.15 | 15 | 2 |
| HSPC:Chol:HPG 1.85:1:0.15 | 4 | 1 |

EXAMPLE 8

Effect of Charged Lipid Components on Blood/RES Ratios in PEG-PE Liposomes

PEG-PE composed of methoxy PEG, molecular weight 1900 and was derivatized DSPE as described in Example 6. The PEG-PE lipids were formulated with lipids selected from among egg PG (PG), partially hydrogenated egg PC (PHEPC), and cholesterol (Chol), as indicated in the FIG. 6. The two formulations shown in the figure contained about 4.7 mole percent (triangles) or 14 mole percent (circles) PG. The lipids were prepared as MLV's, sized to 0.1 micron as in Example 4.

Figure 6:
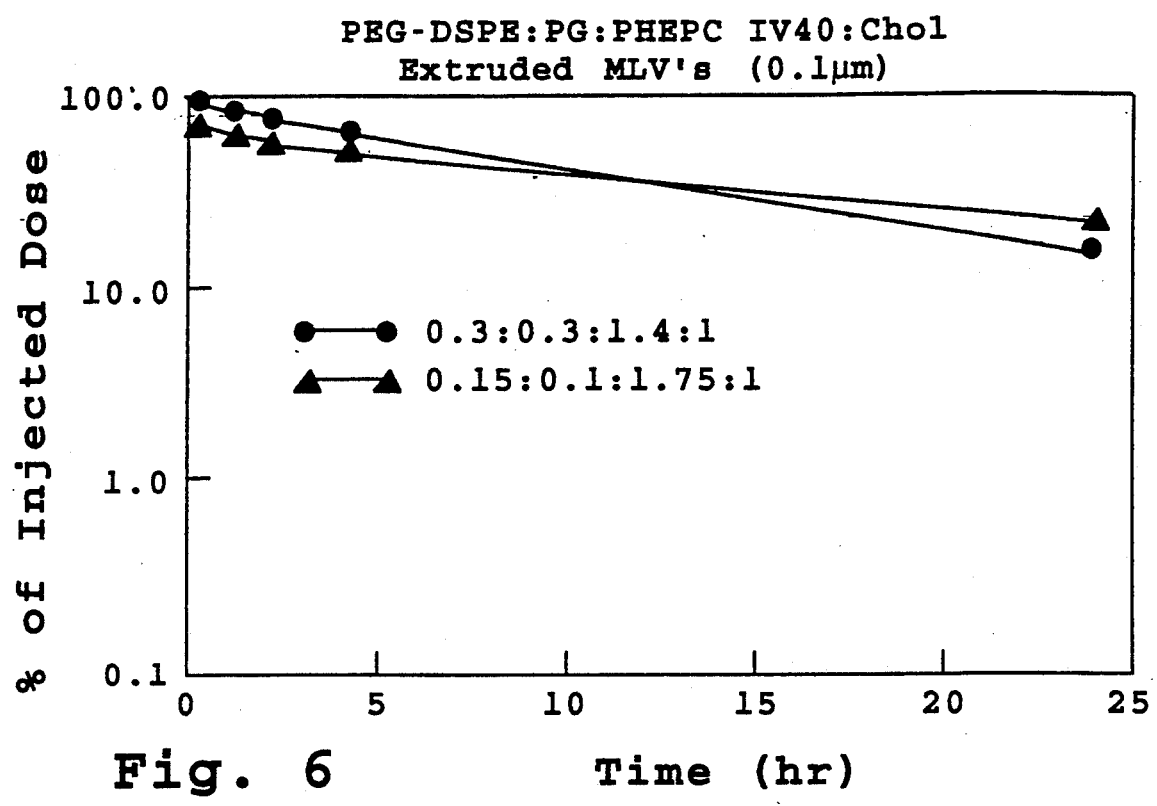
FIG. 6 is a plot of liposome retention time on the blood, expressed in terms of percent injected dose as a function of hours after IV injection, for PEG-PE liposomes containing different amounts of phosphatidyl glycerol.

The percent of injected liposome dose present 0.25, 1, 2, 4, and 24 hours after injection are plotted for both formulations in FIG. 6. As seen, the percent PG in the composition had little or no effect on liposome retention in the bloodstream. The rate of loss of encapsulated marker seen is also similar to that observed for similarly prepared liposomes containing no PG.

Although the invention has been described and illustrated with respect to particular derivatized lipid compounds, liposome compositions, and use, it will be apparent that a variety of modifications and changes may be made without departing from the invention.

It is claimed:

1. A liposome composition for use in delivering a compound via the bloodstream comprising
   liposomes composed of vesicle-forming lipids and between 1-20 mole percent of an amphipathic, vesicle-forming lipid derivatized with a polyethyleneglycol, and containing the compound in liposome-entrapped form, and
   characterized by a blood level, 24 hours after intravenous injection, which is severalfold times that of the liposomes in the absence of the derivatized lipid.

2. The composition of claim 1, wherein the liposomes have a selected average size in the size range between about 0.05 and 0.5 microns.

3. The composition of claim 2, wherein the polyethyleneglycol has a molecular weight is between about 1,000 to 5,000 daltons.

4. The composition of claim 2, wherein the amphipathic lipid is a phospholipid having a polar head group at which the polyethyleneglycol is derivatized, and the liposomes are characterized by a blood circulation lifetime, as measured by the percent liposome marker retained in the blood 24 hours after intravenous injection of the liposomes, which is greater than about 5 percent of the total amount administered.

5. The composition of claim 4, wherein the amphipathic lipid is a phospholipid and the liposomes are characterized by a blood circulation lifetime, as measured by the percent liposome marker retained in the blood 24 hours after intravenous injection of the liposomes, which is greater than about 10 percent of the total amount administered.

6. The composition of claim 4, wherein the phospholipid is phosphatidylethanolamine, and the polyethyleneglycol is coupled to the phospholipid through a lipid amine group.

7. The composition of claim 5, wherein the phospholipid contains acyl chains which are predominantly 18-carbon acyl chains with at least one unsaturated bond.

8. The composition of claim 7, wherein the phospholipid is a phosphatidylethanolamine, and the polyethyleneglycol is coupled to the phospholipid through a lipid amine group.

9. The composition of claim 1, wherein the liposomes contain 10-40 mole percent cholesterol, 40-85 mole percent neutral phospholipid, and 5-15 mole percent phospholipid derivatized with polyethyleneglycol.

10. The composition of claim 1, which is characterized by a blood/RES ratio, 24 hours after intravenous administration, which is at least about tenfold greater than that of the same liposomes in the absence of the derivatized amphipathic lipid.

11. The composition of claim 10, wherein the vesicle-forming lipids making up the liposomes are selected to produce a selected rate of release of the drug from the liposomes circulating in the bloodstream.

12. The composition of claim 11, for the treatment of malignancy, wherein the drug is an amphipathic antitumor compound.

13. The composition of claim 12, wherein the drug is doxorubicin or a pharmacologically acceptable analog or salt thereof.

14. The composition of claim 1, wherein the polyalkylether is linked to the amphipathic lipid through an esterase-or peptidase-sensitive linkage.

15. The composition of claim 1, wherein the liposomes include a surface-bound ligand which is effective to bind specifically and with high affinity to ligand-binding molecules carried on the surface of specific cells circulating in the bloodstream.

16. The composition of claim 15, wherein the surface-bound ligand is an antibody effective to bind specifically and with high affinity to an antigen which is expressed in a cell in the bloodstream in a disease state.

17. The composition of claim 15, wherein the surface-bound ligand is CD4 peptide which is effective to bind to HIV-infected T cell or B cells.

18. A method of producing a severalfold increase in the blood-circulation time of intravenously administered liposomes formed of vesicle-forming lipids and containing an entrapped compound, as measured by the percent liposome marker retained in the blood 24 hours after intravenous injection, substantially independent of the degree of saturation of said vesicle-forming lipids, comprising
   forming the liposomes to include between about 1-20 mole percent an amphipathic, vesicle-forming lipid derivatized with a polyethyleneglycol.

19. The method of claim 18, wherein the liposomes have a selected average size in the size range between about 0.05 and 0.5 microns.

20. The method of claim 18, for increasing the blood-circulation time of intravenously administered liposomes, as measured by the percent liposome marker retained in the blood 24 hours after intravenous injection of the liposomes, to a level which is greater than about 10 percent of the total amount of lipid administered, wherein the amphipathic lipid is a phospholipid, and the polyethyleneglycol has a molecular weight between about 1,000 to 5,000 daltons.

21. The method of claim 18, wherein adding is effective to enhance the blood circulation lifetime 24 hours after intravenous administration, by at least about tenfold over that observed with the same liposomes in the absence of the derivatized amphipathic lipid.

22. A method of administering a compound intravenously, to achieve a level of compound in the bloodstream, 24 hours after drug administration, which is at least about 5 percent of the total amount of compound administered, comprising preparing a suspension of liposomes composed of vesicle-forming lipids and between 1-20 mole percent of an amphipathic, vesicle-forming lipid derivatized with a polyethyleneglycol, and the compound, in liposome-entrapped form, and intravenously administering an amount of the suspension containing a pharmacologically acceptable amount of the drug.

23. The method of claim 22, wherein the polyethyleneglycol has a molecular weight of between about 1,000 and 5,000 daltons.

24. The method of claim 22, wherein the vesicle-forming lipid is a phospholipid, and the level of compound in the bloodstream, 24 hours after liposome administration, is at least about 10 percent of the total compound administered.

25. A method of delivering a drug selectively to a target tissue containing surface-bound tissue-specific ligand-bind molecules, comprising preparing a suspension of liposomes containing between 1-20 mole percent of an vesicle-forming lipid derivatized with a polyethyleneglycol, a surface-bound ligand effective to bind specifically and with high affinity to said ligand-binding molecule, and the drug, in liposome-entrapped form, and intravenously administering an amount of the suspension containing a pharmacologically acceptable amount of the drug.

26. The method of claim 25, wherein the polyethyleneglycol has a molecular weight of between about 1,000 and 5,000 daltons.

27. The method of claim 26, wherein the vesicle-forming lipid is a phospholipid.

28. The method of claim 25, wherein the target tissue is a solid tumor carrying a tumor specific antigen, and the ligand is an antibody specific against such antigen.

29. The method of claim 25, wherein the target tissue is a solid tumor, and the drug is doxorubicin or a pharmacologically acceptable analog or salt thereof.

30. A method of enhancing the uptake, by the reticuloendothelial system, of cells carrying surface-specific ligand-binding molecules which are characteristic of a disease state, comprising preparing a suspension of liposomes containing between 1-20 mole percent of an vesicle-forming lipid derivatized with a polyethyleneglycol, and a surface-bound ligand effective to bind specifically and with high affinity to said ligand-binding molecule, and administering said suspension intravenously.

31. The method of claim 30, wherein the polyethyleneglycol has a molecular weight of between about 1,000 and 5,000 daltons.

32. The method of claim 30, wherein the vesicle-forming lipid is a phospholipid.

33. The method of claim 30, wherein the cells are HIV-infected T-cells or B cells and the surface-bound D4 peptide.

* * * * *